(12) United States Patent
Serrero et al.

(10) Patent No.: US 10,184,032 B2
(45) Date of Patent: Jan. 22, 2019

(54) METHOD FOR PREPARING A CHITOSAN-BASED MATRIX COMPRISING A FIBER REINFORCEMENT MEMBER

(71) Applicant: Sofradim Production, Trévoux (FR)

(72) Inventors: Aurelie Serrero, Lyons (FR); Mylene Desorme, Villeurbanne (FR)

(73) Assignee: Sofradim Production, Trevoux (FR)

( * ) Notice: Subject to any disclaimer, the term of this patent is extended or adjusted under 35 U.S.C. 154(b) by 111 days.

(21) Appl. No.: 15/003,975

(22) Filed: Jan. 22, 2016

(65) Prior Publication Data
US 2016/0237228 A1 Aug. 18, 2016

(30) Foreign Application Priority Data
Feb. 17, 2015 (EP) .................................. 15305236

(51) Int. Cl.
| | | |
|---|---|---|
| C08K 7/02 | (2006.01) |
| C08J 5/04 | (2006.01) |
| A61L 27/20 | (2006.01) |
| A61L 27/18 | (2006.01) |
| A61K 31/722 | (2006.01) |
| C08B 37/08 | (2006.01) |
| C08L 5/08 | (2006.01) |
| A61L 27/56 | (2006.01) |

(52) U.S. Cl.
CPC ............. *C08J 5/046* (2013.01); *A61K 31/722* (2013.01); *A61L 27/18* (2013.01); *A61L 27/20* (2013.01); *A61L 27/56* (2013.01); *C08B 37/003* (2013.01); *C08L 5/08* (2013.01); *C08J 2305/08* (2013.01)

(58) Field of Classification Search
CPC .................................. C08J 5/046; C08L 5/08
See application file for complete search history.

(56) References Cited

U.S. PATENT DOCUMENTS

| | | |
|---|---|---|
| 1,187,158 A | 6/1916 | Mcginley |
| 3,054,406 A | 9/1962 | Usher |
| 3,118,294 A | 1/1964 | Van Laethem |
| 3,124,136 A | 3/1964 | Usher |
| 3,272,204 A | 9/1966 | Charles et al. |
| 3,276,448 A | 10/1966 | Usher |
| 3,320,649 A | 5/1967 | Naimer |
| 3,364,200 A | 1/1968 | Ashton et al. |
| 3,570,482 A | 3/1971 | Emoto et al. |
| 3,718,725 A | 2/1973 | Hamano |
| 4,006,747 A | 2/1977 | Kronenthal et al. |
| 4,060,081 A | 11/1977 | Yannas et al. |
| 4,173,131 A | 11/1979 | Pendergrass et al. |
| 4,193,137 A | 3/1980 | Heck |
| 4,248,064 A | 2/1981 | Odham |
| 4,294,241 A | 10/1981 | Miyata |
| 4,307,717 A | 12/1981 | Hymes et al. |
| 4,338,800 A | 7/1982 | Matsuda |
| 4,476,697 A | 10/1984 | Schafer et al. |
| 4,487,865 A | 12/1984 | Balazs et al. |
| 4,500,676 A | 2/1985 | Balazs et al. |
| 4,511,653 A | 4/1985 | Play et al. |
| 4,527,404 A | 7/1985 | Nakagaki et al. |
| 4,591,501 A | 5/1986 | Cioca |
| 4,597,762 A | 7/1986 | Walter et al. |
| 4,603,695 A | 8/1986 | Ikada et al. |
| 4,631,932 A | 12/1986 | Sommers |
| 4,670,014 A | 6/1987 | Huc et al. |
| 4,709,562 A | 12/1987 | Matsuda |
| 4,748,078 A | 5/1988 | Doi et al. |
| 4,759,354 A | 7/1988 | Quarfoot |
| 4,769,038 A | 9/1988 | Bendavid et al. |
| 4,796,603 A | 1/1989 | Dahlke et al. |
| 4,813,942 A | 3/1989 | Alvarez |
| 4,841,962 A | 6/1989 | Berg et al. |
| 4,854,316 A | 8/1989 | Davis |
| 4,925,294 A | 5/1990 | Geshwind et al. |
| 4,931,546 A | 6/1990 | Tardy et al. |
| 4,942,875 A | 7/1990 | Hlavacek et al. |

(Continued)

FOREIGN PATENT DOCUMENTS

| | | |
|---|---|---|
| CA | 1317836 C | 5/1993 |
| CN | 201879864 U | 6/2011 |

(Continued)

OTHER PUBLICATIONS

Doillon, C.J., et al., "Collagen-based wound dressings: Control of the pore structure and morphology," J. Biomed. Mater. Res., Oct. 1986, pp. 1219-1228, vol. 20(8).

Schoof, H. et al., Control of Pore Structure and Size in Freeze-Dried Collagen Sponges, Journal of Biomedical Materials Research, May 2001, pp. 352-357, vol. 58, No. 4.

Ellouali, M. et al., "Antitumor Activity of Low Molecular Weight Fucans Extracted from Brown Seaweed Ascophyllum Nodosum," Anticancer Res., Nov.-Dec. 1993, pp. 2011-2020, 12 (6A).

(Continued)

*Primary Examiner* — Hannah J Pak (57) ABSTRACT

The present invention relates to a method for preparing a chitosan-based matrix comprising the following steps:

a) two separate chitosan porous layers obtained from lyophilization of layers of one or more solutions of chitosan are provided, b) the chitosan porous layers of a) are neutralized and washed, c) a face of each chitosan porous layer is acidified with an acid, d) a fiber reinforcement member is provided and positioned between the two acidified faces of the two chitosan porous layers, e) the two chitosan porous layers and the fiber reinforcement member are let to dry to obtain a matrix having the fiber reinforcement member embedded therein. The invention also relates to an implant comprising a matrix obtained according to such a method.

24 Claims, 1 Drawing Sheet

(56) References Cited

U.S. PATENT DOCUMENTS

| | | | |
|---|---|---|---|
| 4,948,540 | A | 8/1990 | Nigam |
| 4,950,483 | A | 8/1990 | Ksander et al. |
| 4,970,298 | A | 11/1990 | Silver et al. |
| 4,976,737 | A | 12/1990 | Leake |
| 5,002,551 | A | 3/1991 | Linsky et al. |
| 5,015,584 | A | 5/1991 | Brysk |
| 5,116,357 | A | 5/1992 | Eberbach |
| 5,147,374 | A | 9/1992 | Fernandez |
| 5,162,430 | A | 11/1992 | Rhee et al. |
| 5,171,273 | A | 12/1992 | Silver et al. |
| 5,176,692 | A | 1/1993 | Wilk et al. |
| 5,192,301 | A | 3/1993 | Kamiya et al. |
| 5,195,542 | A | 3/1993 | Gazielly et al. |
| 5,196,185 | A | 3/1993 | Silver et al. |
| 5,201,745 | A | 4/1993 | Tayot et al. |
| 5,201,764 | A | 4/1993 | Kelman et al. |
| 5,206,028 | A | 4/1993 | Li |
| 5,217,493 | A | 6/1993 | Raad et al. |
| 5,254,133 | A | 10/1993 | Seid |
| 5,256,418 | A | 10/1993 | Kemp et al. |
| 5,258,000 | A | 11/1993 | Gianturco |
| 5,263,983 | A | 11/1993 | Yoshizato et al. |
| 5,304,595 | A | 4/1994 | Rhee et al. |
| 5,306,500 | A | 4/1994 | Rhee et al. |
| 5,324,775 | A | 6/1994 | Rhee et al. |
| 5,328,955 | A | 7/1994 | Rhee et al. |
| 5,334,527 | A | 8/1994 | Brysk |
| 5,339,657 | A | 8/1994 | McMurray |
| 5,350,583 | A | 9/1994 | Yoshizato et al. |
| 5,356,432 | A | 10/1994 | Rutkow et al. |
| 5,368,549 | A | 11/1994 | McVicker |
| 5,368,602 | A | 11/1994 | de la Torre |
| 5,370,650 | A | 12/1994 | Tovey et al. |
| 5,376,375 | A | 12/1994 | Rhee et al. |
| 5,376,376 | A | 12/1994 | Li |
| 5,397,331 | A | 3/1995 | Himpens et al. |
| 5,399,361 | A | 3/1995 | Song et al. |
| 5,413,791 | A | 5/1995 | Rhee et al. |
| 5,425,740 | A | 6/1995 | Hutchinson, Jr. |
| 5,428,022 | A | 6/1995 | Palefsky et al. |
| 5,433,996 | A | 7/1995 | Kranzler et al. |
| 5,441,491 | A | 8/1995 | Verschoor et al. |
| 5,441,508 | A | 8/1995 | Gazielly et al. |
| 5,456,693 | A | 10/1995 | Conston et al. |
| 5,456,711 | A | 10/1995 | Hudson |
| 5,466,462 | A | 11/1995 | Rosenthal et al. |
| 5,480,644 | A | 1/1996 | Freed |
| 5,487,895 | A | 1/1996 | Dapper et al. |
| 5,490,984 | A | 2/1996 | Freed |
| 5,512,291 | A | 4/1996 | Li |
| 5,512,301 | A | 4/1996 | Song et al. |
| 5,514,181 | A | 5/1996 | Light et al. |
| 5,522,840 | A | 6/1996 | Krajicek |
| 5,523,348 | A | 6/1996 | Rhee et al. |
| 5,536,656 | A | 7/1996 | Kemp et al. |
| 5,543,441 | A | 8/1996 | Rhee et al. |
| 5,565,210 | A | 10/1996 | Rosenthal et al. |
| 5,567,806 | A | 10/1996 | Abdul-Malak et al. |
| 5,569,273 | A | 10/1996 | Titone et al. |
| RE35,399 | E | 12/1996 | Eisenberg |
| 5,593,441 | A | 1/1997 | Lichtenstein et al. |
| 5,595,621 | A | 1/1997 | Light et al. |
| 5,601,571 | A | 2/1997 | Moss |
| 5,607,474 | A | 3/1997 | Athanasiou et al. |
| 5,607,590 | A | 3/1997 | Shimizu |
| 5,614,587 | A | 3/1997 | Rhee et al. |
| 5,618,551 | A | 4/1997 | Tardy et al. |
| 5,634,931 | A | 6/1997 | Kugel |
| 5,639,796 | A | 6/1997 | Lee |
| 5,665,391 | A | 9/1997 | Lea |
| 5,667,839 | A | 9/1997 | Berg |
| 5,676,967 | A | 10/1997 | Williams et al. |
| 5,681,568 | A | 10/1997 | Goldin et al. |
| 5,686,090 | A | 11/1997 | Schilder et al. |
| 5,686,115 | A | 11/1997 | Vournakis et al. |
| 5,690,675 | A | 11/1997 | Sawyer et al. |
| 5,695,525 | A | 12/1997 | Mulhauser et al. |
| 5,697,978 | A | 12/1997 | Sgro |
| 5,700,476 | A | 12/1997 | Rosenthal et al. |
| 5,700,477 | A | 12/1997 | Rosenthal et al. |
| 5,702,416 | A | 12/1997 | Kieturakis et al. |
| 5,709,934 | A | 1/1998 | Bell et al. |
| 5,711,960 | A | 1/1998 | Shikinami |
| 5,716,409 | A | 2/1998 | Debbas |
| 5,720,981 | A | 2/1998 | Eisinger |
| 5,732,572 | A | 3/1998 | Litton |
| 5,743,917 | A | 4/1998 | Saxon |
| 5,749,895 | A | 5/1998 | Sawyer et al. |
| 5,752,974 | A | 5/1998 | Rhee et al. |
| 5,766,246 | A | 6/1998 | Mulhauser et al. |
| 5,766,631 | A | 6/1998 | Arnold |
| 5,769,864 | A | 6/1998 | Kugel |
| 5,771,716 | A | 6/1998 | Schlussel |
| 5,785,983 | A | 7/1998 | Furlan et al. |
| 5,800,541 | A | 9/1998 | Rhee et al. |
| 5,814,328 | A | 9/1998 | Gunasekaran |
| 5,833,705 | A | 11/1998 | Ken et al. |
| 5,840,011 | A | 11/1998 | Landgrebe et al. |
| 5,861,034 | A | 1/1999 | Taira et al. |
| 5,863,984 | A | 1/1999 | Doillon et al. |
| 5,869,080 | A | 2/1999 | McGregor et al. |
| 5,871,767 | A | 2/1999 | Dionne et al. |
| 5,876,444 | A | 3/1999 | Lai |
| 5,891,558 | A | 4/1999 | Bell et al. |
| 5,899,909 | A | 5/1999 | Claren et al. |
| 5,906,937 | A | 5/1999 | Sugiyama et al. |
| 5,910,149 | A | 6/1999 | Kuzmak |
| 5,911,731 | A | 6/1999 | Pham et al. |
| 5,916,225 | A | 6/1999 | Kugel |
| 5,919,232 | A | 7/1999 | Chaffringeon et al. |
| 5,919,233 | A | 7/1999 | Knopf et al. |
| 5,919,574 | A | 7/1999 | Hoagland |
| 5,922,026 | A | 7/1999 | Chin |
| 5,931,165 | A | 8/1999 | Reich et al. |
| 5,942,278 | A | 8/1999 | Hagedorn et al. |
| 5,962,136 | A | 10/1999 | Dewez et al. |
| 5,972,022 | A | 10/1999 | Huxel |
| RE36,370 | E | 11/1999 | Li |
| 5,993,844 | A | 11/1999 | Abraham et al. |
| 5,994,325 | A | 11/1999 | Roufa et al. |
| 5,997,895 | A | 12/1999 | Narotam et al. |
| 6,001,895 | A | 12/1999 | Harvey et al. |
| 6,008,292 | A | 12/1999 | Lee et al. |
| 6,015,844 | A | 1/2000 | Harvey et al. |
| 6,039,686 | A | 3/2000 | Kovac |
| 6,042,534 | A | 3/2000 | Gellman et al. |
| 6,042,592 | A | 3/2000 | Schmitt |
| 6,043,089 | A | 3/2000 | Sugiyama et al. |
| 6,051,425 | A | 4/2000 | Morota et al. |
| 6,056,688 | A | 5/2000 | Benderev et al. |
| 6,056,970 | A | 5/2000 | Greenawalt et al. |
| 6,057,148 | A | 5/2000 | Sugiyama et al. |
| 6,063,396 | A | 5/2000 | Kelleher |
| 6,066,776 | A | 5/2000 | Goodwin et al. |
| 6,066,777 | A | 5/2000 | Benchetrit |
| 6,071,292 | A | 6/2000 | Makower et al. |
| 6,077,281 | A | 6/2000 | Das |
| 6,080,194 | A | 6/2000 | Pachence et al. |
| 6,083,522 | A | 7/2000 | Chu et al. |
| 6,090,116 | A | 7/2000 | D'Aversa et al. |
| 6,113,623 | A | 9/2000 | Sgro |
| 6,120,539 | A | 9/2000 | Eldridge et al. |
| 6,132,765 | A | 10/2000 | DiCosmo et al. |
| 6,143,037 | A | 11/2000 | Goldstein et al. |
| 6,153,292 | A | 11/2000 | Bell et al. |
| 6,162,962 | A | 12/2000 | Hinsch et al. |
| 6,165,488 | A | 12/2000 | Tardy et al. |
| 6,171,318 | B1 | 1/2001 | Kugel et al. |
| 6,174,320 | B1 | 1/2001 | Kugel et al. |
| 6,176,863 | B1 | 1/2001 | Kugel et al. |
| 6,179,872 | B1 | 1/2001 | Bell et al. |
| 6,180,848 | B1 | 1/2001 | Flament et al. |
| 6,197,325 | B1 | 3/2001 | MacPhee et al. |
| 6,197,934 | B1 | 3/2001 | DeVore et al. |

(56) References Cited

U.S. PATENT DOCUMENTS

| | | | |
|---|---|---|---|
| 6,197,935 B1 | 3/2001 | Doillon et al. |
| 6,210,439 B1 | 4/2001 | Firmin et al. |
| 6,214,020 B1 | 4/2001 | Mulhauser et al. |
| 6,221,109 B1 | 4/2001 | Geistlich et al. |
| 6,224,616 B1 | 5/2001 | Kugel |
| 6,231,879 B1 † | 5/2001 | Li |
| 6,241,768 B1 | 6/2001 | Agarwal et al. |
| 6,258,124 B1 | 7/2001 | Darois et al. |
| 6,262,332 B1 | 7/2001 | Ketharanathan |
| 6,264,702 B1 | 7/2001 | Ory et al. |
| 6,267,772 B1 | 7/2001 | Mulhauser et al. |
| 6,270,530 B1 | 8/2001 | Eldridge et al. |
| 6,277,397 B1 | 8/2001 | Shimizu |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,079 B1 | 10/2001 | Trabucco |
| 6,306,424 B1 | 10/2001 | Vyakarnam et al. |
| 6,312,474 B1 | 11/2001 | Francis et al. |
| 6,319,264 B1 | 11/2001 | Tormala et al. |
| 6,328,686 B1 | 12/2001 | Kovac |
| 6,334,872 B1 | 1/2002 | Termin et al. |
| 6,383,201 B1 | 5/2002 | Dong |
| 6,391,060 B1 | 5/2002 | Ory et al. |
| 6,391,333 B1 | 5/2002 | Li et al. |
| 6,391,939 B2 | 5/2002 | Tayot et al. |
| 6,408,656 B1 | 6/2002 | Ory et al. |
| 6,410,044 B1 | 6/2002 | Chudzik et al. |
| 6,413,742 B1 | 7/2002 | Olsen et al. |
| 6,425,924 B1 | 7/2002 | Rousseau |
| 6,428,978 B1 | 8/2002 | Olsen et al. |
| 6,436,030 B2 | 8/2002 | Rehil |
| 6,440,167 B2 | 8/2002 | Shimizu |
| 6,443,964 B1 | 9/2002 | Ory et al. |
| 6,447,551 B1 | 9/2002 | Goldmann |
| 6,447,802 B2 | 9/2002 | Sessions et al. |
| 6,448,378 B2 | 9/2002 | DeVore et al. |
| 6,451,032 B1 | 9/2002 | Ory et al. |
| 6,451,301 B1 | 9/2002 | Sessions et al. |
| 6,454,787 B1 | 9/2002 | Maddalo et al. |
| 6,477,865 B1 | 11/2002 | Matsumoto |
| 6,479,072 B1 | 11/2002 | Morgan et al. |
| 6,485,503 B2 | 11/2002 | Jacobs et al. |
| 6,500,464 B2 | 12/2002 | Ceres et al. |
| 6,500,777 B1 | 12/2002 | Wiseman et al. |
| 6,509,031 B1 | 1/2003 | Miller et al. |
| 6,511,958 B1 | 1/2003 | Atkinson et al. |
| 6,514,286 B1 | 2/2003 | Leatherbury et al. |
| 6,514,514 B1 | 2/2003 | Atkinson et al. |
| 6,540,773 B2 | 4/2003 | Dong |
| 6,541,023 B1 | 4/2003 | Andre et al. |
| 6,548,077 B1 | 4/2003 | Gunasekaran |
| 6,554,855 B1 | 4/2003 | Dong |
| 6,559,119 B1 | 5/2003 | Burgess et al. |
| 6,566,345 B2 | 5/2003 | Miller et al. |
| 6,575,988 B2 | 6/2003 | Rousseau |
| 6,576,019 B1 | 6/2003 | Atala |
| 6,596,002 B2 | 7/2003 | Therin et al. |
| 6,596,304 B1 | 7/2003 | Bayon et al. |
| 6,599,323 B2 | 7/2003 | Melican et al. |
| 6,599,524 B2 | 7/2003 | Li et al. |
| 6,599,690 B1 | 7/2003 | Abraham et al. |
| 6,610,006 B1 | 8/2003 | Amid et al. |
| 6,613,348 B1 | 9/2003 | Jain |
| 6,616,685 B2 | 9/2003 | Rousseau |
| 6,623,963 B1 | 9/2003 | Muller et al. |
| 6,630,414 B1 | 10/2003 | Matsumoto |
| 6,637,437 B1 | 10/2003 | Hungerford et al. |
| 6,638,284 B1 | 10/2003 | Rousseau et al. |
| 6,645,226 B1 | 11/2003 | Jacobs et al. |
| 6,652,594 B2 | 11/2003 | Francis et al. |
| 6,652,595 B1 | 11/2003 | Nicolo |
| 6,653,450 B1 | 11/2003 | Berg et al. |
| 6,656,206 B2 | 12/2003 | Corcoran et al. |
| 6,660,280 B1 | 12/2003 | Allard et al. |
| 6,669,735 B1 | 12/2003 | Pelissier |
| 6,670,018 B2 | 12/2003 | Fujita et al. |
| 6,682,760 B2 | 1/2004 | Noff et al. |
| 6,685,714 B2 | 2/2004 | Rousseau |
| 6,699,287 B2 † | 3/2004 | Son |
| 6,706,684 B1 | 3/2004 | Bayon et al. |
| 6,706,690 B2 | 3/2004 | Reich et al. |
| 6,712,859 B2 | 3/2004 | Rousseau et al. |
| 6,719,795 B1 | 4/2004 | Cornwall et al. |
| 6,723,335 B1 | 4/2004 | Moehlenbruck et al. |
| 6,726,660 B2 | 4/2004 | Hessel et al. |
| 6,730,299 B1 | 5/2004 | Tayot et al. |
| 6,736,823 B2 | 5/2004 | Darois et al. |
| 6,736,854 B2 | 5/2004 | Vadurro et al. |
| 6,737,371 B1 | 5/2004 | Planck et al. |
| 6,743,435 B2 | 6/2004 | DeVore et al. |
| 6,746,458 B1 | 6/2004 | Cloud |
| 6,752,834 B2 | 6/2004 | Geistlich et al. |
| 6,755,868 B2 | 6/2004 | Rousseau |
| 6,773,723 B1 | 8/2004 | Spiro et al. |
| 6,783,554 B2 | 8/2004 | Amara et al. |
| 6,790,213 B2 | 9/2004 | Cherok et al. |
| 6,790,454 B1 | 9/2004 | Abdul Malak et al. |
| 6,800,082 B2 | 10/2004 | Rousseau |
| 6,833,408 B2 | 12/2004 | Sehl et al. |
| 6,835,336 B2 | 12/2004 | Watt |
| 6,852,330 B2 | 2/2005 | Bowman et al. |
| 6,869,938 B1 | 3/2005 | Schwartz et al. |
| 6,872,227 B2 | 3/2005 | Sump et al. |
| 6,893,653 B2 | 5/2005 | Abraham et al. |
| 6,896,904 B2 | 5/2005 | Spiro et al. |
| 6,926,723 B1 | 8/2005 | Mulhauser et al. |
| 6,936,276 B2 | 8/2005 | Spiro et al. |
| 6,939,562 B2 | 9/2005 | Spiro et al. |
| 6,949,625 B2 | 9/2005 | Tayot |
| 6,966,918 B1 | 11/2005 | Schuldt-Hempe et al. |
| 6,971,252 B2 | 12/2005 | Therin et al. |
| 6,974,679 B2 | 12/2005 | Andre et al. |
| 6,974,862 B2 | 12/2005 | Ringeisen et al. |
| 6,977,231 B1 | 12/2005 | Matsuda |
| 6,984,392 B2 | 1/2006 | Bechert et al. |
| 6,988,386 B1 | 1/2006 | Okawa et al. |
| 7,011,688 B2 | 3/2006 | Gryska et al. |
| 7,021,086 B2 | 4/2006 | Ory et al. |
| 7,022,358 B2 | 4/2006 | Eckmayer et al. |
| 7,025,063 B2 | 4/2006 | Snitkin et al. |
| 7,041,868 B2 | 5/2006 | Greene et al. |
| 7,060,103 B2 | 6/2006 | Carr, Jr. et al. |
| RE39,172 E | 7/2006 | Bayon et al. |
| 7,070,558 B2 | 7/2006 | Gellman et al. |
| 7,087,065 B2 | 8/2006 | Ulmsten et al. |
| 7,094,261 B2 | 8/2006 | Zotti et al. |
| 7,098,315 B2 | 8/2006 | Schaufler |
| 7,101,381 B2 | 9/2006 | Ford et al. |
| 7,115,220 B2 | 10/2006 | Dubson et al. |
| 7,156,804 B2 | 1/2007 | Nicolo |
| 7,156,858 B2 | 1/2007 | Schuldt-Hempe et al. |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,252,837 B2 | 8/2007 | Guo et al. |
| 7,279,177 B2 | 10/2007 | Looney et al. |
| 7,331,199 B2 | 2/2008 | Ory et al. |
| 7,393,319 B2 | 7/2008 | Merade et al. |
| 7,556,598 B2 | 7/2009 | Rao |
| 7,594,921 B2 | 9/2009 | Browning |
| 7,614,258 B2 | 11/2009 | Cherok et al. |
| 7,615,065 B2 | 11/2009 | Priewe et al. |
| 7,662,169 B2 | 2/2010 | Wittmann |
| 7,670,380 B2 | 3/2010 | Cauthen, III |
| 7,682,381 B2 | 3/2010 | Rakos et al. |
| 7,709,017 B2 | 5/2010 | Tayot |
| 7,718,556 B2 | 5/2010 | Matsuda et al. |
| 7,732,354 B2 | 6/2010 | Fricke et al. |
| 7,785,334 B2 | 8/2010 | Ford et al. |
| 7,789,888 B2 | 9/2010 | Bartee et al. |

(56) References Cited

U.S. PATENT DOCUMENTS

| | | |
|---|---|---|
| 7,799,767 B2 | 9/2010 | Lamberti et al. |
| 7,806,905 B2 | 10/2010 | Ford et al. |
| 7,824,420 B2 | 11/2010 | Eldridge et al. |
| 7,828,854 B2 | 11/2010 | Rousseau et al. |
| 7,900,484 B2 | 3/2011 | Cherok et al. |
| 7,931,695 B2 | 4/2011 | Ringeisen |
| 8,052,759 B2 | 11/2011 | Dupic et al. |
| 8,079,023 B2 | 12/2011 | Chen |
| 8,100,924 B2 | 1/2012 | Browning |
| 8,123,817 B2 | 2/2012 | Intoccia et al. |
| 8,142,515 B2 | 3/2012 | Therin et al. |
| 8,157,821 B2 | 4/2012 | Browning |
| 8,157,822 B2 | 4/2012 | Browning |
| 8,182,545 B2 | 5/2012 | Cherok et al. |
| 8,197,837 B2 | 6/2012 | Jamiolkowski et al. |
| 8,206,632 B2 | 6/2012 | Rousseau et al. |
| 8,215,310 B2 | 7/2012 | Browning |
| 8,317,872 B2 | 11/2012 | Adams |
| 8,323,675 B2 | 12/2012 | Greenawalt |
| 8,343,232 B2 | 1/2013 | Adzich et al. |
| 8,366,787 B2 | 2/2013 | Brown et al. |
| 8,435,307 B2 | 5/2013 | Paul |
| 8,470,355 B2 | 6/2013 | Skalla et al. |
| 8,562,633 B2 | 10/2013 | Cully et al. |
| 8,574,627 B2 | 11/2013 | Martakos et al. |
| 8,709,094 B2 | 4/2014 | Stad et al. |
| 8,734,471 B2 | 5/2014 | Deitch |
| 8,753,360 B2 | 6/2014 | Gleiman et al. |
| 8,758,800 B2 | 6/2014 | Stopek et al. |
| 8,784,294 B2 | 7/2014 | Goddard |
| 8,814,887 B2 | 8/2014 | Walther et al. |
| 8,828,092 B2 | 9/2014 | Toso et al. |
| 8,834,864 B2 | 9/2014 | Odar et al. |
| 8,846,060 B2 | 9/2014 | Archibald et al. |
| 8,865,215 B2 | 10/2014 | Ladet et al. |
| 8,877,233 B2 | 11/2014 | Obermiller et al. |
| 8,911,504 B2 | 12/2014 | Mathisen et al. |
| 8,920,370 B2 | 12/2014 | Sholev et al. |
| 8,956,373 B2 | 2/2015 | Ford et al. |
| 8,962,006 B2 | 2/2015 | Bayon et al. |
| 8,968,762 B2 | 3/2015 | Ladet et al. |
| 8,979,935 B2 | 3/2015 | Lozier et al. |
| 9,034,357 B2 | 5/2015 | Stopek |
| 9,113,993 B2 | 8/2015 | Lee |
| 9,211,175 B2 | 12/2015 | Stopek et al. |
| 9,216,075 B2 | 12/2015 | Bailly et al. |
| 2002/0087174 A1 | 7/2002 | Capello |
| 2002/0095218 A1 | 7/2002 | Carr et al. |
| 2003/0086975 A1 | 5/2003 | Ringeisen |
| 2003/0114937 A1 | 6/2003 | Leatherbury et al. |
| 2003/0133967 A1 | 7/2003 | Ruszczak et al. |
| 2003/0225355 A1 | 12/2003 | Butler |
| 2004/0034373 A1 | 2/2004 | Schuldt-Hempe et al. |
| 2004/0054376 A1 | 3/2004 | Ory et al. |
| 2004/0059356 A1 | 3/2004 | Gingras |
| 2004/0101546 A1 | 5/2004 | Gorman et al. |
| 2005/0002893 A1 | 1/2005 | Goldmann |
| 2005/0021058 A1 | 1/2005 | Negro |
| 2005/0085924 A1 | 4/2005 | Darois et al. |
| 2005/0113849 A1 | 5/2005 | Popadiuk et al. |
| 2005/0137512 A1 | 6/2005 | Campbell et al. |
| 2005/0142161 A1 | 6/2005 | Freeman et al. |
| 2005/0148963 A1 | 7/2005 | Brennan |
| 2005/0175659 A1 | 8/2005 | MacOmber et al. |
| 2005/0232979 A1 | 10/2005 | Shoshan |
| 2005/0267521 A1 | 12/2005 | Forsberg |
| 2005/0288691 A1 | 12/2005 | Leiboff |
| 2006/0116696 A1 | 6/2006 | Odermatt et al. |
| 2006/0135921 A1 | 6/2006 | Wiercinski et al. |
| 2006/0147501 A1 | 7/2006 | Hillas et al. |
| 2006/0216320 A1 | 9/2006 | Kitazono et al. |
| 2006/0252981 A1 | 11/2006 | Matsuda et al. |
| 2006/0253203 A1 | 11/2006 | Alvarado |
| 2006/0282103 A1 | 12/2006 | Fricke et al. |
| 2007/0088391 A1 | 4/2007 | McAlexander et al. |
| 2007/0129736 A1 | 6/2007 | Solecki |
| 2007/0198040 A1 | 8/2007 | Buevich et al. |
| 2007/0299538 A1 | 12/2007 | Roeber |
| 2008/0091276 A1 | 4/2008 | Deusch et al. |
| 2008/0109017 A1 | 5/2008 | Herweck et al. |
| 2008/0113001 A1 | 5/2008 | Herweck et al. |
| 2008/0172071 A1 | 7/2008 | Barker |
| 2008/0255593 A1 | 10/2008 | St-Germain |
| 2009/0035341 A1 | 2/2009 | Wagener et al. |
| 2009/0036996 A1 | 2/2009 | Roeber |
| 2009/0068250 A1 | 3/2009 | Gravagna et al. |
| 2009/0105526 A1 | 4/2009 | Piroli Torelli et al. |
| 2009/0163936 A1 | 6/2009 | Yang et al. |
| 2009/0187197 A1 | 7/2009 | Roeber et al. |
| 2009/0192530 A1 | 7/2009 | Adzich et al. |
| 2009/0204129 A1 | 8/2009 | Fronio |
| 2009/0216338 A1 | 8/2009 | Gingras et al. |
| 2009/0270999 A1 | 10/2009 | Brown |
| 2009/0281558 A1 | 11/2009 | Li |
| 2009/0318752 A1 | 12/2009 | Evans et al. |
| 2010/0104608 A1 | 4/2010 | Abuzaina et al. |
| 2010/0318108 A1 | 12/2010 | Datta et al. |
| 2011/0015760 A1 | 1/2011 | Kullas |
| 2011/0081677 A1 | 4/2011 | Luo et al. |
| 2011/0144667 A1 | 6/2011 | Horton et al. |
| 2011/0190795 A1 | 8/2011 | Hotter et al. |
| 2011/0238094 A1 | 9/2011 | Thomas et al. |
| 2011/0251699 A1 | 10/2011 | Ladet |
| 2011/0257666 A1 | 10/2011 | Ladet et al. |
| 2011/0311632 A1 | 12/2011 | Roorda et al. |
| 2012/0016388 A1 | 1/2012 | Houard et al. |
| 2012/0029537 A1 | 2/2012 | Mortarino |
| 2012/0065727 A1 | 3/2012 | Reneker et al. |
| 2012/0082712 A1 | 4/2012 | Stopek et al. |
| 2012/0116425 A1 | 5/2012 | Intoccia et al. |
| 2012/0150204 A1 | 6/2012 | Mortarino et al. |
| 2012/0165937 A1 | 6/2012 | Montanari et al. |
| 2012/0179175 A1 | 7/2012 | Hammell |
| 2012/0179176 A1 | 7/2012 | Wilson et al. |
| 2012/0197415 A1 | 8/2012 | Montanari et al. |
| 2014/0044861 A1 | 2/2014 | Boey et al. |
| 2014/0364684 A1 | 12/2014 | Lecuivre |
| 2017/0189574 A1* | 7/2017 | Jaillon ............... A61L 15/325 |
| 2017/0290956 A1* | 10/2017 | Vestberg ............. A61L 31/042 |

FOREIGN PATENT DOCUMENTS

| | | |
|---|---|---|
| DE | 19544162 C1 | 4/1997 |
| DE | 19718903 A1 | 12/1997 |
| DE | 19751733 A1 | 12/1998 |
| DE | 19832634 A1 | 1/2000 |
| DE | 10019604 A1 | 10/2001 |
| DE | 10120942 A1 | 10/2001 |
| DE | 10043396 C1 | 6/2002 |
| EP | 0194192 A1 | 9/1986 |
| EP | 0248544 A1 | 12/1987 |
| EP | 0263360 A2 | 4/1988 |
| EP | 0276890 A2 | 8/1988 |
| EP | 0372969 A1 | 6/1990 |
| EP | 0531742 A1 | 3/1993 |
| EP | 544485 A1 | 6/1993 |
| EP | 0552576 A1 | 7/1993 |
| EP | 0611561 A1 | 8/1994 |
| EP | 614650 A2 | 9/1994 |
| EP | 0621014 A1 | 10/1994 |
| EP | 0625891 A1 | 11/1994 |
| EP | 0637452 A1 | 2/1995 |
| EP | 0664132 A1 | 7/1995 |
| EP | 0705878 A2 | 4/1996 |
| EP | 0719527 A1 | 7/1996 |
| EP | 0774240 A1 | 5/1997 |
| EP | 0797962 A2 | 10/1997 |
| EP | 0800791 A1 | 10/1997 |
| EP | 827724 A2 | 3/1998 |
| EP | 0836838 A1 | 4/1998 |
| EP | 0847727 A1 | 6/1998 |
| EP | 0876808 A1 | 11/1998 |
| EP | 0895762 A2 | 2/1999 |
| EP | 898944 A2 | 3/1999 |

(56) References Cited

FOREIGN PATENT DOCUMENTS

| | | |
|---|---|---|
| EP | 1017415 A1 | 7/2000 |
| EP | 1036545 A2 | 9/2000 |
| EP | 1052319 A1 | 11/2000 |
| EP | 1055757 A1 | 11/2000 |
| EP | 1090590 A2 | 4/2001 |
| EP | 1 216 717 A1 | 6/2002 |
| EP | 1 216 718 A1 | 6/2002 |
| EP | 0693523 B1 | 11/2002 |
| EP | 1315468 A2 | 6/2003 |
| EP | 1382728 A1 | 1/2004 |
| EP | 1484070 A1 | 12/2004 |
| EP | 1561480 A2 | 8/2005 |
| EP | 1645232 A1 | 4/2006 |
| EP | 1674048 A1 | 6/2006 |
| EP | 1691606 A1 | 8/2006 |
| EP | 1782848 A2 | 5/2007 |
| EP | 2229918 A1 | 9/2010 |
| EP | 2522376 A2 | 11/2012 |
| FR | 2244853 A1 | 4/1975 |
| FR | 2257262 A1 | 8/1975 |
| FR | 2 308 349 A1 | 11/1976 |
| FR | 2453231 A1 | 10/1980 |
| FR | 2612392 A1 | 9/1988 |
| FR | 2715309 A1 | 7/1995 |
| FR | 2715405 A1 | 7/1995 |
| FR | 2 724 563 A1 | 3/1996 |
| FR | 2730406 A1 | 8/1996 |
| FR | 2744906 A1 | 8/1997 |
| FR | 2766698 A1 | 2/1999 |
| FR | 2771622 A1 | 6/1999 |
| FR | 2773057 A1 | 7/1999 |
| FR | 2774277 A1 | 8/1999 |
| FR | 2779937 A1 | 12/1999 |
| FR | 2859624 A1 | 3/2005 |
| FR | 2863277 A1 | 6/2005 |
| FR | 2876020 A1 | 4/2006 |
| FR | 2884706 A1 | 10/2006 |
| FR | 2929834 A1 | 10/2009 |
| FR | 2953709 A1 | 6/2011 |
| GB | 1174814 A | 12/1969 |
| GB | 2 051 153 A | 1/1981 |
| GB | 2306110 A | 4/1997 |
| JP | H0332677 A | 2/1991 |
| JP | H05237128 A | 9/1993 |
| JP | H09137380 A | 5/1997 |
| JP | H11146888 A | 6/1999 |
| JP | 2008538300 A | 10/2008 |
| JP | 2011078767 A | 4/2011 |
| NO | 9310731 A1 | 6/1993 |
| NO | 96/08277 A1 | 3/1996 |
| WO | 89/02445 A1 | 3/1989 |
| WO | 89/08467 A1 | 9/1989 |
| WO | 9009769 A1 | 9/1990 |
| WO | 90/12551 A1 | 11/1990 |
| WO | 92/06639 A2 | 4/1992 |
| WO | 92/20349 A1 | 11/1992 |
| WO | 93/11805 A1 | 6/1993 |
| WO | 93/18174 A1 | 9/1993 |
| WO | 94/17747 A1 | 8/1994 |
| WO | 95/07666 A1 | 3/1995 |
| WO | 95/18638 A1 | 7/1995 |
| WO | 95/32687 A1 | 12/1995 |
| WO | 96/03091 A1 | 2/1996 |
| WO | 96/09795 A1 | 4/1996 |
| WO | 96/14805 A1 | 5/1996 |
| WO | 96/41588 A1 | 12/1996 |
| WO | 97/35533 A1 | 10/1997 |
| WO | 98/35632 A1 | 8/1998 |
| WO | 98/49967 A1 | 11/1998 |
| WO | 99/05990 A1 | 2/1999 |
| WO | 99/06079 A1 | 2/1999 |
| WO | 99/06080 A1 | 2/1999 |
| WO | 99/51163 A1 | 10/1999 |
| WO | 00/16821 A1 | 3/2000 |
| WO | 00/67663 A1 | 11/2000 |
| WO | 01/15625 A1 | 3/2001 |
| WO | 01/80773 A1 | 11/2001 |
| WO | 01/81667 A1 | 11/2001 |
| WO | 02/007648 A1 | 1/2002 |
| WO | 0217853 A2 | 3/2002 |
| WO | 02/078568 A1 | 10/2002 |
| WO | 03/002168 A1 | 1/2003 |
| WO | 2004004600 A1 | 1/2004 |
| WO | 2004071349 A2 | 8/2004 |
| WO | 2004078120 A2 | 9/2004 |
| WO | 2004103212 A1 | 12/2004 |
| WO | 200511280 A1 | 2/2005 |
| WO | 2005013863 A2 | 2/2005 |
| WO | 2005018698 A1 | 3/2005 |
| WO | 2005048708 A1 | 6/2005 |
| WO | 2005105172 A1 | 11/2005 |
| WO | 2006018552 A1 | 2/2006 |
| WO | 2006023444 A2 | 3/2006 |
| WO | 2007/042281 A2 | 4/2007 |
| WO | 2007048099 A2 | 4/2007 |
| WO | 2009031035 A2 | 3/2009 |
| WO | 2009031047 A2 | 3/2009 |
| WO | 2009071998 A2 | 6/2009 |
| WO | 2009156866 A2 | 12/2009 |
| WO | 2010043978 A2 | 4/2010 |
| WO | 2011007062 A1 | 1/2011 |
| WO | 2011026987 A1 | 3/2011 |
| WO | 2011038740 A1 | 4/2011 |
| WO | 2014020132 A1 | 2/2014 |

OTHER PUBLICATIONS

Malette, W. G. et al., "Chitosan, A New Hemostatic," Ann Th. Surg., Jul. 1983, pp. 55-58, 36.

Langenbech, M. R. et al., "Comparison of biomaterials in the early postoperative period," Surg Enclose., May 2003, pp. 1105-1109, 17 (7).

Bracco, P. et al., "Comparison of polypropylene and polyethylene terephthalate (Dacron) meshes for abdominal wall hernia repair: A chemical and morphological study," Hernia, 2005, pp. 51-55, 9 (1), published online Sep. 2004.

Klinge, U. et al., "Foreign Body Reaction to Meshes Used for the Repair of Abdominal Wall Hernias," Eur J. Surg, Sep. 1999, pp. 665-673, 165.

Logeart, D. et al., "Fucans, sulfated polysaccharides extracted from brown seaweeds, inhibit vascular smooth muscle cell proliferation. II. Degradation and molecular weight effect," Eur. J. Cell. Biol., Dec. 1997, pp. 385-390, 74(4).

Haneji, K. et al., "Fucoidan extracted from Cladosiphon Okamuranus Tokida Induces Apoptosis of Human T-cell Leukemia Virus Type 1-Infected T-Cell Lines and Primary Adult T-Cell Leukemia Cells," Nutrition and Cancer, 2005, pp. 189-201, 52(2), published online Nov. 2009.

Junge, K. et al., "Functional and Morphologic Properties of a Modified Mesh for Inguinal Hernia Repair," World J. Burg., Sep. 2002, pp. 1472-1480, 26.

Klinge, U. et al., "Functional and Morphological Evaluation of a Low-Weight, Monofilament Polypropylene Mesh for Hernia Repair," J. Biomed. Mater. Res., Jan. 2002, pp. 129-136, 63.

Welty, G. et al., "Functional impairment and complaints following incisional hernia repair with different polypropylene meshes," Hernia, Aug. 2001; pp. 142-147, 5.

Varum, K. et al., "In vitro degradation rates of partially N-acetylated chitosans in human serum," Carbohydrate Research, Mar. 1997, pp. 99-101, 299.

Haroun-Bouhedja, F. et al., "In Vitro Effects of Fucans on MDA-MB231 Tumor Cell Adhesion and Invasion," Anticancer Res., Jul.-Aug. 2002, pp. 2285-2292, 22(4).

Scheidbach, H. et al., "In vivo studies comparing the biocompatibility of various polypropylene meshes and their handling properties during endoscopic total extraperitoneal (TEP) patchplasty: An experimental study in pigs," Surg. Endosc., Feb. 2004, pp. 211-220,18(2).

(56) References Cited

OTHER PUBLICATIONS

Blondin, C. et al., "Inhibition of Complement Activation by Natural Sulfated Polysaccharides (Fucans) from Brown Seaweed," Molecular Immuol., Mar. 1994, pp. 247-253, 31(4).
Zvyagintseva, T. et al., "Inhibition of complement activation by water-soluble polysaccharides of some far-eastern brown seaweeds," Comparative Biochem and Physiol, Jul. 2000, pp. 209-215,126(3).
Rosen, M. et al., "Laparoscopic component separation in the single-stage treatment of infected abdominal wall prosthetic removal," Hernia, 2007, pp. 435-440, 11, published online Jul. 2007.
Amid, P., "Lichtenstein tension-free hernioplasty: Its inception, evolution, and principles," Hernia, 2004; pp. 1-7, 8, published online Sep. 2003.
Boisson-Vidal, C. et al., "Neoangiogenesis Induced by Progenitor Endothelial Cells: Effect of Fucoidan From Marine Algae," Cardiovascular & Hematological Agents in Medicinal Chem., Jan. 2007, pp. 67-77, 5(1).
O'Dwyer, P. et al., "Randomized clinical trial assessing impact of a lightweight or heavyweight mesh on chronic pain after inguinal hernia repair," Br. J. Surg., Feb. 2005, pp. 166-170, 92(2).
Muzzarelli, R. et al., "Reconstruction of parodontal tissue with chitosan," Biomaterials, Nov. 1989, pp. 598-604, 10.
Haroun-Bouhedja, F. et al., "Relationship between sulfate groups and biological activities of fucans," Thrombosis Res., Dec. 2000, pp. 453-459, 100(5).
Blondin, C. et al., "Relationships between chemical characteristics and anticomplementary activity of fucans," Biomaterials, Mar. 1996, pp. 597-603, 17(6).
Strand, S. et al., "Screening of Chitosans and Conditions for Bacterial Flocculation," Biomacromolecules, Mar. 2001, 126-133, 2.
Kanabar, V. et al., "Some structural determinants of the antiproliferative effect of heparin-like molecules on human airway smooth muscle," Br. J. Pharmacol., Oct. 2005, pp. 370-777, 146(3).
Hirano, S. et al., "The blood biocompatibility of chitosan and N-acylchitosans," J. Biomed. Mater. Res., Apr. 1985, 413-417, 19.
Rao, B. et al., "Use of chitosan as a biomaterial: Studies on its safety and hemostatic potential," J. Biomed. Mater. Res., Jan. 1997, pp. 21-28, 34.
Prokop, A. et al., "Water Soluble Polymers for Immunoisolation I: Complex Coacevation and Cytotoxicity," Advances in Polymer Science, Jul. 1998, pp. 1-51, 136.
Collins, R. et al., "Use of collagen film as a dural substitute: Preliminary animal studies," Journal of Biomedical Materials Research, Feb. 1991, pp. 267-276, vol 25.
Preliminary Search Report from French Patent Office dated Dec. 20, 2006, 3 pages.
Lamarque, G. et al, "New Route of Deacetylation of alpha- and beta-Chitins by Means of Freeze-Pump Out-Thaw cycles" Biomacromolecules, May-Jun. 2005, pp. 1380-1388, 6.

Lamarque, G. et al., "Comparative Study of the First Heterogeneous Deacetylation of alpha- and beta-Chitins in a Multistep Process" Biomacromolecules May-Jun. 2004, 992-1001, 5.
Lamarque, G. et al., "Comparative Study of the Second and Third Heterogeneous Deacetylations of alpha- and beta-Chitins in a Multistep Process" Biomacromolecules, Sep.-Oct. 5, 2004, pp. 1899-1907, 5.
Tolaimate, A., et al. "Contribution to the preparation of chitins and chitosans with controlled physico-chemical properties." Polymer, Dec. 2003, pp. 7939-7952, 44 (26).
O'Brien, F. J. et al., "Influence of freezing rate on pore structure in freeze-dried collagen-GAG scaffolds" Biomaterials, Mar. 2004, pp. 1077-1086, vol. 25, Issue 6.
Sarasam A et al, Characterization of chitosan-polycaprolactone blends for tissue engineering applications11, Biomaterials, Elsevier Science Publishers BV., Barking, GB, vol. 26, No. 27, Sep. 1, 2005 (Sep. 1, 2005), pp. 5500-5508.
Fu J et al: Construction of anti-adhesive and antibacterial multilayer films via layer-by-layer assembly of heparin and chitosan11, Biomaterials, Elsevier Science Publishers BV., Barking, GB, vol. 26, No. 33, Nov. 1, 2005 (Nov. 1, 2005), pp. 6684-6692).
Adeline Martin et al: Build-up of an antimicrobial multilayer coating on a textile support based on a methylene blue-poly(cyclodextrin) com11, Biomedical Materials, Institute of Physics Publishing, Bristol, GB, vol. 8, No. 6, Nov. 26, 2013 (Nov. 26, 2013), p. 65006.
Tea Indest et al: Adsorption of Fucoidan and Chitosan Sulfate on Chitosan Modified PET Films Monitored by QCM-D11, Biomacromolecules, vol. 10, No. 3, Mar. 9, 2009 (Mar. 9, 2009), pp. 630-637.
Hong Li et al: Layer-by-layer hyaluronic acid-chitosan coating promoted new collagen ingrowth into a poly(ethylene terephthalate) artificial ligament in a rabbit medical collateral ligament (MCL) reconstruction model11, Journal of Biomaterials Science, Polymer Edition, vol. 24, No. 4, Mar. 1, 2013 (Mar. 1, 2013), pp. 431-446.
Liu et al: "Surface modification of poly(ethylene terephthalate) via hydrolysis and layer-by-layer assembly of chitosan and chondroitin sulfate to construct cytocompatible layer for human endothelial cells", Colloids and Surfaces. Biointerfaces, Elsevier, Amsterdam, NL, vol. 46, No. 2, Dec. 10, 2005 (Dec. 10, 2005), pp. 117-126.
Aiping Z et al: "Blood compatibility of surface-engineered poly-(ethylene terephthalate) via o-carboxymethylchitosan", Colloids and Surfaces. B, Biointerfaces, Elsevier, Amsterdam, NL, vol. 50, No. 2, Jul. 1, 2006 (Jul. 1, 2006), pp. 120-125.
LD Wright et al: PDLA/PLLA and PDLA/PCL nanofibers with a chitosan-based hydrogel in composite scaffolds for tissue engineered cartilage11, Journal of Tissue Engineering and Regenerative Medicine, vol. 8, No. 12, Dec. 1, 2014 (Dec. 1, 2014), pp. 946-954.
Andrea S. Gobin et al: Repair and Regeneration of the Abdominal Wall Musculofascial Defect Using Silk Fibroin-Chitosan Blend11, Tissue Engineering, vol. 12, No. 0, Jan. 1, 2006 (Jan. 1, 2006), p. 3383.

\* cited by examiner
† cited by third party

METHOD FOR PREPARING A CHITOSAN-BASED MATRIX COMPRISING A FIBER REINFORCEMENT MEMBER

CROSS-REFERENCE TO RELATED APPLICATION

This application claims benefit of and priority to European Patent Application Serial No. 15305236.0 filed Feb. 17, 2015, the disclosure of the above-identified application is hereby incorporated by reference in its entirety.

BACKGROUND

Technical Field

The present invention relates to a method for preparing a matrix of chitosan including a fiber reinforcement member sandwiched between two porous layers of chitosan. The present invention further relates to matrices obtained by this method and their use as, or in the manufacture of, wall reinforcement implant that may be used, for example, in the repair, reinforcement or replacement of soft tissues, e.g. treatment of hernias, reconstruction of a wall, such as a visceral or abdominal wall. The implants of the invention may also be used in vitro as a tissue engineering product or support for culturing live cells.

Description of Related Art

Chitosan is a polysaccharide which results from the deacetylation of chitin. Chitin is one of the most widespread natural polysaccharides on earth and is extracted from the exoskeletons of arthropods, from the endoskeletons of cephalopods and also from fungi.

Chitosan has properties, such as biodegradability, bioresorbability, biocompatibility, non-toxicity and mechanical properties, which make it particularly advantageous for medical applications. Thus, chitosan can be incorporated into medical devices as a constituent of implants, for example in the form of a porous structure such as a matrix. Chitosan in fact offers a good compromise, given the desired properties, for an abdominal wall reinforcement implant, namely good biological compatibility and good mechanical properties.

Chitosan matrices are usually obtained by lyophilization of a chitosan solution. Lyophilization involves a first step during which a solution is frozen in a particular structure, and then a second step, during which a controlled pressure is applied in order to cause sublimation of the water present in the frozen structure. At the end of the sublimation step, only the constituents present in the initial solution remain, thus producing a porous structure.

Indeed, the porous structure of such chitosan matrices is of particular interest in the manufacture of surgical implants for many reasons. When the implant is intended to repair a tissue defect, for example in the case of a hernia in the abdominal wall, a porous structure favors cell colonization and therefore reconstruction of the biological tissue.

Wall reinforcement implants, for example for reinforcing the abdominal wall, are widely used in surgery. These implants are intended to treat hernias by temporarily or permanently filling a tissue defect. These implants may show a number of shapes, for example rectangular, circular or oval, depending on the anatomical structure to which they are to adapt. These implants may be made entirely from bioresorbable elements when they are intended to disappear after they have performed their reinforcing function during the period of cellular colonization and tissue rehabilitation. Alternatively, these implants may include, or consist in, non-bioresorbable parts which are intended to remain permanently in the body of the patient.

In addition to exhibit a porosity favourable to cell growth, the structure of an abdominal wall reinforcement implant should at the same time possess mechanical properties allowing it to be easily handleable by the surgeon, to perform its reinforcement function once implanted and to maintain its integrity at least during the time necessary for reconstruction, even when submitted to potential tensions, generated for example either by sutures ensuring the fixation of the implant to the surrounding biological tissue or by the various movements of the patient in his daily life.

Depending on the level of mechanical properties desired for a wall reinforcement implant, it may be useful to reinforce a chitosan matrix obtained by lyophilization of a chitosan solution by combining it with a fiber reinforcement member, such as a mesh.

It is known to lyophilize a chitosan solution in which a fiber reinforcement member such as a mesh is previously immersed in order to obtain a mesh embedded in a chitosan matrix. Anyway, after lyophilization, the chitosan matrices are still very loaded with salts. The matrices must therefore be neutralized before being used as an implant.

It has been observed that the shrinkage of matrices that usually go along with the neutralization of these matrices induces high constraints in the embedded mesh. This phenomenon is detrimental to the use of the resulting matrix as an implant, as the mesh will not behave as expected after implantation.

It would therefore be desirable to implement a method of preparing chitosan matrices having a fiber reinforcement member embedded therein, where the fiber reinforcement member would not be damaged or affected by the preparation method and where the integrity of the matrix would be preserved.

SUMMARY

The present invention relates to a method for preparing a chitosan-based matrix comprising a fiber reinforcement member embedded in said matrix comprising the following steps:
 a) two separate chitosan porous layers obtained from lyophilisation of layers of one or more solution(s) of chitosan are provided,
 b) the chitosan porous layers of a) are neutralized and washed,
 c) a face of each chitosan porous layer is acidified with an acid,
 d) a fiber reinforcement member is provided and positioned between the two acidified faces of the two chitosan porous layers,
 e) the two chitosan porous layers and the fiber reinforcement member are let to dry to obtain a matrix having the fiber reinforcement member embedded therein.

The method according to the invention makes it possible to obtain chitosan-based matrix including a fiber reinforcement member embedded in the matrix, where the matrix shows a good integrity and good mechanical properties. In particular, the fiber reinforcement member of the matrices of the invention is neither damaged nor affected by the preparation method of the matrix. The fiber reinforcement member of the matrices of the invention is not submitted to constraints tending to deform it in either direction. No shrinkage of the fiber reinforcement member is observed in the matrices of the invention.

In particular, the matrices obtained by the method of the invention show a good stability and a good cohesion of the various parts constituting the matrix, namely the two chitosan porous layers and the fiber reinforcement member. In the matrices obtained by the method of the invention, no delamination between the chitosan porous layers and the fiber reinforcement member is observed when immersed in water even after a long exposure time. In the matrices obtained by the method of the invention, the fiber reinforcement member is securely sandwiched between the two porous layers of chitosan.

The chitosan matrices obtained by means of the method according to the invention therefore make it possible to obtain particularly effective surgical implants, for example for reinforcing the abdominal wall. The chitosan matrices obtained by the method of the invention may be used on their own or in combination with another element, such as for example a film, an additional reinforcement member or an additional porous layer.

BRIEF DESCRIPTION OF THE DRAWINGS

The invention and the advantages thereof will emerge more clearly from the detailed description below and the appended figures in which.

DETAILED DESCRIPTION OF EMBODIMENTS

By "chitosan-based matrix" it is intended to mean according to the present application that the major compound of the solution(s) from which the porous layers forming the matrix of the invention are obtained by lyophilisation is chitosan. In embodiments, the solution(s) from which the chitosan porous layers are obtained is/are substantially free of any other polymer. In the present application, by "substantially free of any other polymer" is meant that the solution(s) contain less than 5%, preferably less than 1% in weight of other polymer. In embodiments, the chitosan solution(s) used in the method of the invention is/are free of any other polymer.

According to a first step of the method according to the invention, step a), two separate chitosan porous layers obtained from lyophilisation of layers of one or more solution(s) of chitosan are provided. The two chitosan porous layers may be identical or different in composition. For example, the compositions of the two chitosan porous layers may be different with respect to the concentration of chitosan, and/or to the degree of acetylation of the chitosan used, and/or to the origin of the chitosan used, etc. . . . When it is intended to use two chitosan porous layers having different compositions in the method of the invention, two different chitosan solutions are prepared and each porous layer is obtained from lyophilisation of a layer of the corresponding chitosan solution. Alternatively, when it is intended to use two chitosan porous layers having identical compositions, a single chitosan solution may be prepared. In such a case, the two chitosan porous layers may be obtained either by lyophilisation of two separate layers of the single chitosan solution, or by cutting in two one thicker porous layer obtained by lyophilisation of one appropriate layer of the single chitosan solution.

Chitosan is a biocompatible biopolymer resulting from the deacetylation of chitin. Chitin is extracted from exoskeletons of arthropods such as lobster, crab or shrimp, from the endoskeleton of cephalopods such as squid, or else from fungi. The extraction of chitin involves steps of protein and lipid hydrolysis, of depigmentation and of demineralization. Usually, the protein and lipid hydrolysis is carried out in the presence of sodium hydroxide, the demineralization requiring the use of hydrochloric acid.

Once the chitin has been extracted, the chitosan is obtained by means of a deacetylation step, which consists of hydrolysis of the acetamide groups. This reaction is generally carried out at high temperature in an alkaline solution, for example a solution of sodium hydroxide (NaOH) at 48% in water, at 90° C.

The following publications also describe methods for deacetylation of chitin in order to obtain chitosan: "Lamarque, G., C. Viton, and A. Domard, *New Route of Deacetylation of α- and β-Chitins by Means of Freeze-Pump Out-Thaw Cycles*. Biomacromolecules, 2005. 6(3): p. 1380-1388.", "Lamarque, G., C. Viton, and A. Domard, *Comparative Study of the First Heterogeneous Deacetylation of α- and β-Chitins in a Multistep Process*. Biomacromolecules, 2004. 5(3): p. 992-1001.", "Lamarque, G., C. Viton, and A. Domard, *Comparative Study of the Second and Third Heterogeneous Deacetylations of α- and β-Chitins in a Multistep Process*. Biomacromolecules, 2004. 5(5): p. 1899-1907.", "Tolaimate, A., et al., *Contribution to the preparation of chitins and chitosans with controlled physico-chemical properties*. Polymer, 2003. 44(26): p. 7939-7952."

Chitosans which are suitable as starting materials for the method according to the invention are available from the companies Kitozyme (fungus extract), Heppe Medical chitosan (shrimp or crab extract), Primex (shrimp extract) and Novamatrix (shrimp extract).

Chitosan is a biodegradable compound. The degree of acetylation of chitosan can have an influence on the chitosan degradation kinetics. Thus, depending on the biodegradation kinetics desired for the each chitosan porous layer of the matrix prepared according to the method of the invention, the chitosan used in each porous layer may have a degree of acetylation of 2, 3, 10, 20, 30, 40 or else 50%: the desired degree of acetylation can also be obtained by preparing a mixture of several chitosans having various degrees of acetylation. In particular, the degree of acetylation of the chitosan used for one chitosan porous layer may be different from the degree of acetylation of the chitosan used for the other chitosan porous layer.

The chitosan solutions of step a) of the method according to the invention are generally prepared by solubilization of chitosan in powder form in water. The solutions may be adjusted to the desired pH, for example by adding acetic acid. In embodiments of the method according to the invention, the pH of each chitosan solution is adjusted to a value ranging from 3 to 5, preferably to 3.5, for example by adding acetic acid. Such a pH makes it possible to obtain, in the end, a chitosan-based porous matrix which has good mechanical properties.

In embodiments of the method according to the invention, each solution of step a) is a solution of chitosan in water, the chitosan concentration in said solution ranging from 0.1% to 10%, preferably from 0.5% to 3% and more preferably from 0.8% to 1% by weight, relative to the total weight of the solution.

Such chitosan concentrations make it possible to obtain, in the end, chitosan porous layers/matrices having good mechanical properties. Also preferably, each chitosan solution of the method according to the invention is free of any other polymer. The presence of a polymer other than chitosan in the solution could affect the mechanical or biological properties of the matrices.

Two separate chitosan porous layers are prepared from the lyophilisation of layer(s) of the chitosan solution(s) prepared as described above. When the two separate chitosan porous layers to be used in the method of the invention are of different compositions, two different chitosan solutions are prepared. A part of each solution is poured in a mould in order to form a solution layer. Each mould is in general in the shape of a rectangle having dimensions compatible with the chitosan porous layer to be prepared. Each chitosan porous layer is obtained from lyophilisation of the corresponding solution layer. When it is intended to use two chitosan porous layers of identical compositions, parts of the single chitosan solution may be poured into two moulds in order to form two solution layers. The two separate chitosan porous layers will be obtained from lyophilisation of the two solution layers. Alternatively, a larger volume of the single chitosan solution may be poured in a bigger mould in order to form a thicker solution layer. The two separate chitosan porous layers intended to be used in the method of the invention are then obtained by cutting the thicker porous layer obtained by lyophilisation of the thicker solution layer into two thinner chitosan porous layers.

In the present application, the term "porous layer" is intended to mean a layer which has pores, or gaps, alveoli, holes, orifices, which are evenly or unevenly distributed not only at the surface, but also within the thickness of said layer, and which are more or less interconnected, depending on the lyophilization process used. Such lyophilization processes are known. It is known practice to vary the freezing temperature and speed and also the characteristics of the polymer solution to be lyophilized (pH, concentration, etc.), in this case chitosan, as a function of the structure of the sponge or porous layer that it is desired to obtain (see U.S. Pat. No. 4,970,298; Doillon et al, J Biomed Mater Res, 1986; Schoof, J Biomed Mater Res, 2001; O'Brien et al, Biomaterials, 2004).

According to a second step of the method according to the invention, step b), the chitosan porous layers of step a) are neutralized and washed.

The chitosan porous layers may for example be neutralized by immersion in a neutralizing solution. The neutralizing solution may be a basic solution, such as a NaOH or NH$_4$OH solution in water or in an alcohol such as ethanol. For example, each chitosan porous layer may be dipped during five minutes in about 600-800 mL of neutralizing solution, such as a solution of NaOH 0.5M in pure ethanol.

The neutralized chitosan porous layers are then submitted to one or more washing steps. The washing step makes it possible to eliminate from a chitosan porous layer any salts still remaining in the layer, for instance sodium acetate or ammonium acetate salts.

For example, each neutralized chitosan porous layer is dipped in one or more baths of sterile water until a washing water with a pH close to 7 is obtained.

According to a third step of the method according to the invention, step c), a face of each chitosan porous layer obtained in b) is acidified with an acid. For example, a superficial layer of each chitosan porous layer is acidified with a fine layer of acid. The acidification of the face is preferably limited to a superficial layer of the chitosan porous layer so as not to degrade the chitosan porous layer. The acid is preferably spread out on the face of the chitosan porous layer in a quantity so as to cause a gentle and slight resolubilization of a superficial layer of said face. For example, the thickness of the superficial layer which is acidified may represent up to 5%, preferably up to 2% of the total thickness of the chitosan porous layer.

In embodiments, the face is acidified by spraying a solution of said acid on said face. The spraying may be repeated twice.

In embodiments, the acid is selected from acetic acid, hydrochloric acid, citric acid, sulphuric acid, lactic acid, and mixtures thereof. In embodiments, the acid is acetic acid.

In embodiments, the face is acidified by spraying a solution of acetic acid at 0.1 M on said face, for example twice.

In a fourth step of the method according to the invention, step d), a fiber reinforcement member is provided.

Some suitable non-limiting examples of the fiber reinforcement member include fabrics, meshes, monofilaments, multifilament braids, chopped fibers (sometimes referred to in the art as staple fibers) and combinations thereof.

In embodiments, the fiber reinforcement member is a porous mesh. The fiber reinforcement member may be prepared using any technique known to those skilled in the art, such as knitting, weaving, tatting, knipling or the like. Illustrative examples of suitable meshes include any of those that are presently commercially available for abdominal wall repair. In embodiments where a mesh is used as the fiber reinforcement member, the mesh will bring mechanical properties to the matrix or implant and will aid in affixing the matrix or implant comprising the matrix to the surrounding biological tissue.

Where monofilaments or multifilament braids are used as the reinforcement member, the monofilaments or multifilament braids may be oriented in any desired manner. Where chopped fibers are used as the reinforcement member, the chopped fibers may be oriented in any desired manner. For example, the chopped fibers may be randomly oriented or may be oriented in a common direction. The chopped fibers can thus form a non-woven material, such as a mat or a felt.

The fiber reinforcement member may be made from any biocompatible polymer material. The biocompatible polymer may be synthetic or natural. The biocompatible polymer may be biodegradable, non-biodegradable or a combination of biodegradable and non-biodegradable. The term "biodegradable" as used herein is defined to include both bioabsorbable and bioresorbable materials. By biodegradable, it is meant that the materials decompose, or lose structural integrity under body conditions (e.g., enzymatic degradation or hydrolysis) or are broken down (physically or chemically) under physiologic conditions in the body such that the degradation products are excretable or absorbable by the body.

The biocompatible polymer may be selected from the group consisting of biodegradable polymers, non-biodegradable polymers, and combinations thereof.

In embodiments, the reinforcement member may include at least a non-bioabsorbable material to provide long term tissue support. In other embodiments, the reinforcement member is formed entirely of bioabsorbable material, for example when the implant of the invention is not intended to be a long lasting tissue support.

In embodiments, the biocompatible polymer material is selected from polypropylene (PP), polyester such as polyethylene terephthalates (PET), polyamide, silicone, polyether ether ketone (PEEK), polyarylether ether ketone (PAEK) polylactic acid (PLA), polycaprolactone (PCL), polydioxanone (PDO), trimethylene carbonate (TMC), polyvinyl alcohol (PVA), polyhydroxyalkanoate (PHA), polyglycolic acid (PGA), copolymers of these materials, and mixtures thereof.

In embodiments, the biocompatible polymer material is selected from polypropylene, polyethylene terephthalates and mixtures thereof.

Figure 1:
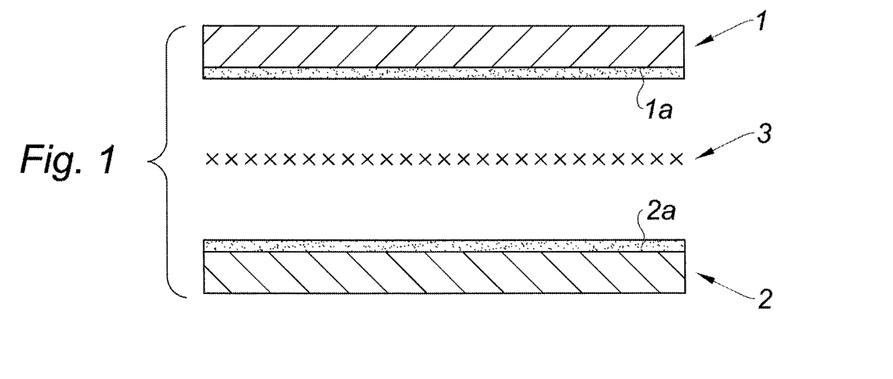
FIG. 1 is a side view of two chitosan porous layers and of a fiber reinforcement member ready to be assembled according to the method of the invention.

The fiber reinforcement member is positioned between the two acidified faces of the chitosan porous layers. With reference to FIG. 1, are shown the two chitosan porous layers (1, 2), each having an acidified superficial layer (1a, 2a) on one face. The fiber reinforcement member 3 is ready to be positioned between the two acidified faces (1a, 2a) of the chitosan porous layers (1, 2). The fiber reinforcement member 3 is brought in contact with the acidified superficial layers (1a, 2a) of the chitosan porous layers (1, 2).

Figure 2:
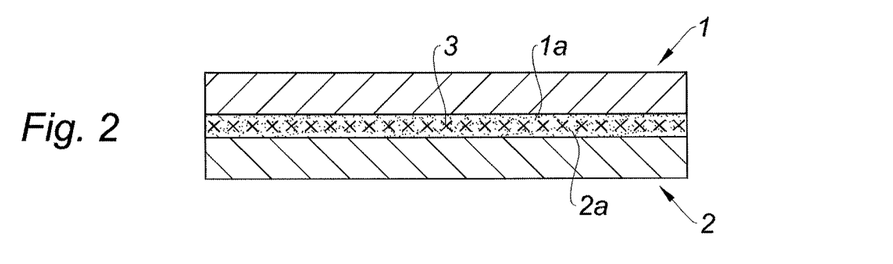
FIG. 2 is a side view of the step showing the two chitosan porous layers and the fiber reinforcement member of FIG. 1 assembled together before the drying step.

The fiber reinforcement 3 is therefore sandwiched between the two chitosan porous layers (1, 2), and imprisoned in the two acidified superficial layers (1a, 2a) which melt together, as shown on FIG. 2. In embodiments, a pressure is applied on the chitosan porous layers (1, 2) in direction of the fiber reinforcement member 3 during and/or after the positioning of the fiber reinforcement member between the two chitosan porous layers. The pressure may be maintained during part or whole of the subsequent drying step. In embodiments, a pressure may be applied towards the fiber reinforcement member when it is put in place between the two chitosan porous layers for a time ranging from a few seconds to a few minutes. For example, a pressure may be applied towards the fiber reinforcement member when it is put in place between the two chitosan porous layers for a time up to about 60 seconds, for example for about 20 seconds.

In embodiments, the pressure applied may range from about 2.5 to about 10 kPa, preferably is about 3.5 kPa.

In a fifth step of the method of the invention, step e), the fiber reinforcement member and the two chitosan porous layers are let to dry.

The drying may take place under a hood for example, for a time ranging from about 8 hours to about 12 hours for instance.

During the drying step, the resolubilized superficial layers (1a, 2a) of the chitosan porous layers which surround the fiber reinforcement member 3 solidify. The fiber reinforcement member 3 eventually strongly adheres to the faces of the chitosan porous layers (1, 2). At the end of the drying step, the two chitosan porous layers (1, 2) and the fiber reinforcement member 3 are securely bound together, as shown on FIG. 3.

Figure 3:
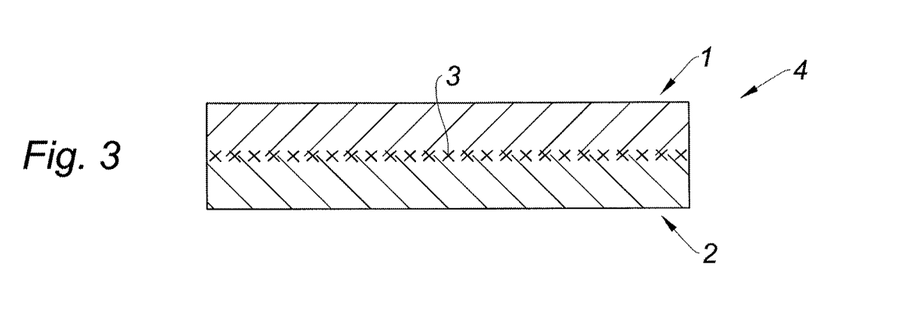
FIG. 3 is a side view of a matrix of the invention obtained after drying of the assembly shown on FIG. 2.

The matrix obtained 4 is under the form of a fiber reinforcement member 3 sandwiched between two porous layers (1, 2) of chitosan, as shown on FIG. 3. The matrix obtained 4 shows an excellent stability. In particular, the matrix 4 obtained by the method of the invention shows no delamination, even after having been immersed in a water bath for three weeks.

In embodiments, in step d) above, the fiber reinforcement member is impregnated with a solution of acid before being positioned between the two acidified faces of the two chitosan porous layers. In embodiments, the solution of acid may be a solution of an acid selected from acetic acid, hydrochloric acid, citric acid, sulphuric acid, lactic acid, and mixtures thereof, and preferably a solution of acetic acid.

In embodiments, the fiber reinforcement member is impregnated with a solution of acetic acid. For example, the fiber reinforcement member is dipped into a solution of acetic acid at 0.1 M. Such embodiments allow obtaining an excellent and homogeneous bonding between the fiber reinforcement member and the two chitosan porous layers.

In embodiments, the chitosan porous layers and the fiber reinforcement member having substantially bidimensional structures, the area of the fiber reinforcement member is smaller than that of each chitosan porous layers. Such embodiments show a very good resistance to natural delamination as well as to provoked delamination.

By "substantially bidimensional structure" is meant in the present application that the structure has one of its three dimensions which is significantly smaller than the two others so that the structure is substantially planar, such as a layer having a small thickness, or a mesh.

For example, the chitosan porous layers may have the same dimensions and may be under the form of rectangular layers having a length L and a width W, and a thickness much smaller than L and W. The fiber reinforcement member may be under the shape of a bidimensional textile having a length $L_F$ and a width $W_F$. In embodiments, the area $L_F \times W_F$ of the fiber reinforcement member is smaller than the area L×W of each chitosan porous layers.

The matrix obtained by the method of the invention can be part of or constitute the whole of a surgical implant, for example for reinforcing the abdominal wall.

Thus, another aspect of the invention relates to a chitosan-based matrix obtained by the method described above.

Another aspect of the invention relates to an implant, in particular for reinforcing the abdominal wall, comprising at least one matrix obtained by means of the method described above.

The invention and the advantages thereof will emerge more clearly from the examples below.

Example 1

1°) Production of Two Separate Chitosan Porous Layers:

Porous layers of chitosan of DA (degree of acetylation) 4% were produced according to the following procedure.

A 1% (w/w) chitosan solution is prepared as follows: 4.70 g of chitosan were first suspended in 445 g sterile water and dissolved under mechanical stirring by adding 1.56 ml of acetic acid to achieve the stoechiometric protonation of free amine groups of D-glucosamine residues. Usually, an excess of 10% of acetic acid is added to enhance the dissolution.

This operation is realized in a STEPHAN unit with mechanical stirring at 300 rpm and room temperature. To avoid any temperature increase, the bowl is equipped with a cooling bath to maintain the room temperature at a temperature T<25° C. The dissolution takes about 2 to 3 hours in these conditions.

After complete dissolution of the polymer, the pH of the chitosan solution is 4.5. The pH is then adjusted to pH 3.5 by addition of 7.5 ml of acetic acid. Solutions of pH 3.5 allow improving the mechanical properties of the resulting chitosan porous layer. The 1% (w/w) chitosan solution is then degassed under static vacuum: such a step allows removing air bubbles that could impact both porosity and mechanical properties of the resulting matrices. For example, the solution is degassed at 150 mbars, 300 rpm and 25° C. for 30 min. 2 or 3 degassing cycles are usually necessary to achieve complete degassing.

121 g of degassed chitosan solution are then poured in a plastic mould of 12 cm×17 cm dimensions in order to form a layer which is freeze-dried in a TELSTAR Lyobeta freeze drier according to a 28 hours cycle, namely a freezing step of about 4 hours and a primary drying step of about 24 hours.

A first chitosan porous layer is obtained. The same procedure is repeated in order to obtain a second chitosan porous layer.

In the present example, the two chitosan porous layers have identical compositions. In other embodiments, the composition of one chitosan porous layer could be different from that of the other chitosan porous layer, in particular regarding the concentration of chitosan and/or the degree of acetylation of chitosan, and/or the origin of the chitosan, etc.

2°) Neutralization of the Chitosan Porous Layers Produced at 1°):

The chitosan porous layers obtained at point 1°) above were neutralized by immersion during 10 minutes into a neutralizing solution of NaOH 0.5M in 96% ethanol. The chitosan porous layers were then washed in sterile water baths during 10 min (typically 1 L/matrix) to remove the excess of sodium hydroxide and residual salts. Washings were repeated until the washing solution reached a neutral pH and a conductivity below 2 µS/cm.

After neutralization, the chitosan porous layers show dimensions of 10 cm×15 cm and were further recut at the following dimensions: 6 cm×4 cm. They have a thickness ranging from about 4 mm to about 5 mm.

3°) Assembling of a Matrix of the Invention:

A fiber reinforcement member under the form of a knit made of polyethylene terephthalate and having dimensions of 6 cm×4 cm is provided.

A face of each chitosan porous layer obtained at point 2°) above is acidified by spraying thereon a fine layer of a solution of acetic acid at a concentration of 0.1 M. The spraying is repeated twice in a homogeneous way. Only a superficial layer of the face is acidified so that the integrity of the chitosan porous layer is preserved. This acidification of the face has as a consequence to resolubilize a superficial layer of said chitosan porous layer. The thickness of the acidified superficial layer represents about 1% of the total thickness of the chitosan porous layer.

The fiber reinforcement member is positioned between the two chitosan porous layers with the acidified faces of the chitosan porous layers directed towards the fiber reinforcement member.

A pressure of about 3.5 kPa is applied on the two chitosan porous layers towards the fiber reinforcement member, by depositing on the chitosan porous layers a mass of 850 g during about 20 seconds.

The mass is then removed and the matrix, made of the fiber reinforcement member sandwiched between the two chitosan porous layers, is let to dry under a hood for about 8-12 hours at room temperature (about 20° C.).

During the drying step, the resolubilized superficial layers of the chitosan porous layers which surround the fiber reinforcement member solidify and eventually imprison the fiber reinforcement member which strongly adheres to the faces of the chitosan porous layers. At the end of the drying step, the two chitosan porous layers and the fiber reinforcement member are securely bound together.

Once the matrix is dried, it is very stable and no delamination of the fiber reinforcement member from the two chitosan porous layers occurs.

The matrix is put in a water bath for 1 hour. No delamination of the fiber reinforcement member from the two chitosan porous layers is observed.

Example 2

A matrix of the invention is prepared in the same manner as in EXAMPLE 1 above, except that the fiber reinforcement member is dipped into a solution of acetic acid at a concentration of 0.1 M prior to be positioned between the two acidified faces of the chitosan porous layers.

The matrix is dried in the same manner as in EXAMPLE 1.

The matrix obtained is very stable and no delamination of the fiber reinforcement member from the two chitosan porous layers occurs.

The matrix is put in a water bath for 1 hour. No delamination of the fiber reinforcement member from the two chitosan porous layers is observed. In addition, if one attempts to delaminate the two chitosan porous layers of the matrix by pulling out in opposite directions the end of each chitosan porous layer, a significant resistance to said delamination is observed: in particular, if two jaws of a holder grasp the opposite chitosan porous layers of the matrix and are then taken away one from the other, the matrix breaks at the place it is grasped by one of the jaws but no delamination is observed between the fiber reinforcement member and the chitosan porous layers.

Example 3

A matrix of the invention is prepared in the same manner as in EXAMPLE 1 above, except that the fiber reinforcement member has the following dimensions: 4 cm×4 cm.

The matrix obtained is very stable and no delamination of the fiber reinforcement member from the two chitosan porous layers occurs.

The matrix is put in a water bath for 1 hour. No delamination of the fiber reinforcement member from the two chitosan porous layers is observed.

Example 4

A matrix of the invention is prepared in the same manner as in EXAMPLE 2 above, except that the fiber reinforcement member has the following dimensions: 4 cm×4 cm.

The matrix obtained is very stable and no delamination of the fiber reinforcement member from the two chitosan porous layers occurs.

The matrix is put in a water bath for 1 hour. No delamination of the fiber reinforcement member from the two chitosan porous layers is observed.

In addition, if one attempts to delaminate the two chitosan porous layers of the matrix by pulling out in opposite directions the end of each chitosan porous layer, a significant resistance to delamination and to tearing is observed. In particular, in such conditions, a greater resistance to delamination and to tearing is observed with the matrix of the present example compared to the matrices of Examples 1-3.

Matrices of the invention prepared in the four examples above may be used on their own as wall reinforcement implants to be implanted in a patient for hernia repair for example. Alternatively, these matrices may be used in combination with a anti-adhesion barrier film or with one or more additional matrices/porous layers in order to manufacture a composite surgical implant.

What is claimed is:

1. A method for preparing a chitosan-based matrix comprising a fiber reinforcement member embedded in the matrix comprising:
 a) providing one or more solutions including chitosan,
 b) obtaining two separate chitosan porous layers from lyophilisation of the one or more solutions of chitosan,
 c) neutralizing the chitosan porous layers of b),
 d) washing the chitosan porous layers of c), e) applying an acid to a face of each of the chitosan porous layers of d), f) positioning a fiber reinforcement member between the two acidified faces of the two chitosan porous layers of e), g) drying the two chitosan porous layers and the fiber reinforcement member of f) to obtain a matrix having the fiber reinforcement member embedded therein.

2. The method according to claim 1, wherein providing one or more solutions including chitosan comprises a solution of chitosan in water, the chitosan including a concentration in the solution ranging from 0.1% to 10% by weight, relative to a total weight of the solution.

3. The method according to claim 1, wherein providing one or more solutions including chitosan comprises a solution of chitosan in water, the chitosan including a concentration in the solution ranging from 0.5% to 3% by weight, relative to a total weight of the solution.

4. The method according to claim 1, wherein providing one or more solutions including chitosan comprises a solution of chitosan in water, the chitosan including a concentration in the solution ranging from 0.8% to 1% by weight, relative to a total weight of the solution.

5. The method according to claim 1, further comprising adjusting a pH of the one or more solutions in a) to a value ranging from 3 to 5.

6. The method according to claim 1, further comprising adjusting a pH of the one or more solutions in a) to a value of 3.5.

7. The method according to claim 5, wherein adjusting a pH of the one or more solutions in a) comprises adding acetic acid to the one or more of solutions.

8. The method according to claim 1, wherein applying an acid according to e) comprises spraying a solution of the acid on the face.

9. The method according to claim 1, wherein the acid according to e) is selected from the group consisting of acetic acid, hydrochloric acid, citric acid, sulphuric acid, lactic acid, and mixtures thereof.

10. The method according to claim 1, wherein the acid according to e) comprises acetic acid.

11. The method according to claim 10, wherein applying the acid according to e) comprises spraying a solution of acetic acid at 0.1 M on the face of each of the chitosan porous layers.

12. The method according to claim 11, wherein the spraying is repeated twice.

13. The method of claim 1, further comprising impregnating the fiber reinforcement member with a solution of an acid before being positioned between the two acidified faces of the two chitosan porous layers of e).

14. The method according to claim 13, wherein the solution of the acid comprises an acid selected from the group consisting of acetic acid, hydrochloric acid, citric acid, sulphuric acid, lactic acid, and mixtures thereof.

15. The method according to claim 13, wherein the solution of the acid comprises acetic acid.

16. The method according to claim 15, wherein the solution of the acid comprises a solution of acetic acid at 0.1 M.

17. The method according to claim 1, wherein the chitosan porous layers and the fiber reinforcement member have substantially bidimensional structures, and an area of the fiber reinforcement member is smaller than an area of each chitosan porous layer.

18. The method according to claim 1, wherein the fiber reinforcement member is a porous mesh.

19. The method according to claim 1, further comprising applying a pressure on the chitosan porous layers in a direction of the fiber reinforcement member during and/or after the positioning a fiber reinforcement member between the two acidified faces of the two chitosan porous layers of e).

20. The method according to claim 1, wherein neutralizing the chitosan porous layers of b) comprises immersing the chitosan porous layers of a) in a basic solution.

21. The method according to claim 20, wherein the basic solution comprises NaOH or $NH_4OH$ in water or an alcohol.

22. The method according to claim 1, wherein washing the chitosan porous layers of c) comprises dipping the chitosan porous layers of c) in one or more baths of sterile water until a washing water with a pH close to 7 is obtained.

23. The method according to claim 1, wherein applying an acid to a face of each of the chitosan porous layers of d) further comprises obtaining a superficial layer on the face of each of the chitosan porous layers so as to cause a resolubilization of the superficial layer of each face.

24. The method according to claim 23, wherein the superficial layer comprises a thickness up to 5% of a total thickness of each chitosan porous layer.

* * * * *